US008661895B2

(12) United States Patent
Stafford et al.

(10) Patent No.: US 8,661,895 B2
(45) Date of Patent: Mar. 4, 2014

(54) CARRYING CASES FOR MEDICAL DEVICES THAT USE ANALYTE TEST STRIPS AND METHODS OF USING THE SAME

(75) Inventors: Gary Ashley Stafford, Hayward, CA (US); Mark Kent Sloan, Redwood City, CA (US); Johnny Chang, San Bruno, CA (US); Jessica Ching, Berkeley, CA (US); Mina Min Leung, Mountain View, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 339 days.

(21) Appl. No.: 12/980,325

(22) Filed: Dec. 28, 2010

(65) Prior Publication Data
US 2011/0154889 A1 Jun. 30, 2011

Related U.S. Application Data

(60) Provisional application No. 61/290,856, filed on Dec. 29, 2009.

(51) Int. Cl.
*G01D 11/24* (2006.01)
*G01L 19/14* (2006.01)
*G01P 1/02* (2006.01)

(52) U.S. Cl.
USPC ............................................ 73/431; D3/203.8

(58) Field of Classification Search
USPC .............................. 73/431; 206/545, 569, 570
See application file for complete search history.

(56) References Cited

U.S. PATENT DOCUMENTS

| | | | |
|---|---|---|---|
| 4,040,547 A | 8/1977 | Dickey | |
| 4,411,267 A | 10/1983 | Heyman | |
| 4,419,794 A | 12/1983 | Horton et al. | |
| 4,514,276 A | 4/1985 | Covington et al. | |
| 4,934,817 A * | 6/1990 | Gassenhuber | 356/446 |
| D310,167 S | 8/1990 | Reber | |
| 5,054,170 A | 10/1991 | Otrusina | |
| 5,201,858 A | 4/1993 | Otrusina | |
| D348,355 S | 7/1994 | Scheid et al. | |
| 5,370,622 A | 12/1994 | Livingston et al. | |
| 5,385,282 A | 1/1995 | Chen | |
| 5,452,497 A | 9/1995 | Peng | |
| 5,472,317 A | 12/1995 | Field et al. | |
| D366,957 S | 2/1996 | Scheid et al. | |
| 5,613,236 A | 3/1997 | Tajima et al. | |
| 5,620,120 A | 4/1997 | Tien | |
| 5,709,012 A | 1/1998 | Ebashi | |
| 5,806,146 A | 9/1998 | Chen | |
| 5,850,954 A | 12/1998 | Dong-Joo | |
| D408,878 S | 4/1999 | Patten | |
| D409,374 S | 5/1999 | Laba et al. | |
| 5,906,031 A | 5/1999 | Jensen | |
| 5,988,577 A | 11/1999 | Phillips et al. | |
| D418,119 S | 12/1999 | Rowell | |
| 6,059,156 A | 5/2000 | Lehtinen | |
| 6,105,923 A | 8/2000 | Robertson et al. | |

(Continued)

FOREIGN PATENT DOCUMENTS

WO WO-03/049597 6/2003

*Primary Examiner* — Lisa Caputo
*Assistant Examiner* — Roger Hernandez-Prewitt
(74) *Attorney, Agent, or Firm* — Jackson & Co., LLP

(57) ABSTRACT

Carrying cases for medical devices and components thereof are provided. Also provided are methods for carrying medical devices and for medical testing.

20 Claims, 6 Drawing Sheets

(56) References Cited

U.S. PATENT DOCUMENTS

| | | |
|---|---|---|
| 6,176,401 B1 | 1/2001 | Lim |
| 6,283,348 B1 | 9/2001 | Wang |
| 6,293,962 B1 | 9/2001 | Bishay |
| D457,308 S | 5/2002 | Infanti |
| 6,443,340 B1 | 9/2002 | Chung et al. |
| 6,470,535 B1 | 10/2002 | Mayne et al. |
| 6,752,299 B2 | 6/2004 | Shetler et al. |
| 6,781,522 B2 * | 8/2004 | Sleva et al. ............... 340/870.1 |
| 7,129,836 B2 | 10/2006 | Lawson et al. |
| 7,303,726 B2 | 12/2007 | McAllister et al. |
| 7,722,536 B2 * | 5/2010 | Goodnow .................... 600/365 |
| 2003/0106940 A1 | 6/2003 | Bukowski |
| 2004/0155079 A1 | 8/2004 | Shetler et al. |
| 2005/0101875 A1 | 5/2005 | Semler et al. |
| 2005/0137573 A1 | 6/2005 | McLaughlin |
| 2006/0094986 A1 | 5/2006 | Neel et al. |
| 2006/0293577 A1 * | 12/2006 | Morrison et al. ............ 600/365 |
| 2007/0179404 A1 | 8/2007 | Escutia et al. |
| 2008/0060955 A1 | 3/2008 | Goodnow |
| 2009/0048501 A1 | 2/2009 | Goodnow et al. |
| 2009/0226050 A1 * | 9/2009 | Hughes ......................... 382/124 |
| 2010/0052293 A1 | 3/2010 | Brooks et al. |
| 2010/0076290 A1 | 3/2010 | Bernstein et al. |
| 2010/0331653 A1 | 12/2010 | Stafford |

* cited by examiner

CARRYING CASES FOR MEDICAL DEVICES THAT USE ANALYTE TEST STRIPS AND METHODS OF USING THE SAME

RELATED APPLICATION

The present application claims the benefit of U.S. provisional application No. 61/290,856 filed Dec. 29, 2009 entitled "Carrying Cases for Medical Devices and Methods", the disclosure of which is incorporated herein by reference for all purposes.

FIELD OF THE DISCLOSURE

The present disclosure is directed to carrying cases for holding medical devices. In particular embodiments, the present disclosure is directed to carrying cases for holding and carrying portable medical devices such as, but not limited to, one or more components of a continuous glucose monitoring system.

BACKGROUND

Analytical analyte testers and meters are often used in chemistry and medicine to assay for one or more analytes, e.g., to determine the presence and/or concentration of a biological analyte of interest. For example, such analytical testers and meters are used to monitor glucose in diabetic patients and lactate during critical care events.

A variety of medical devices have been developed so that an individual may monitor their health outside of a doctor's office or hospital environment. For example, the home monitoring of analytes by a user has become increasingly important for disease prevention and management. In one instance, the level of glucose and/or other analytes, such as lactate or oxygen, in certain individuals is vitally important to their health. High or low levels of glucose or other analytes may have detrimental effects. The monitoring of glucose is particularly important to individuals with diabetes, e.g., in some instances a diabetic must determine when insulin is needed to be administered to reduce glucose levels in their bodies or when additional glucose is needed to raise the level of glucose in their bodies.

Conventional techniques for monitoring blood glucose levels include the use of an in vitro analyte tester and associated reader. This in vitro technique involves the periodic obtaining of a biological sample, the application of that sample to an in vitro analyte test strip, and the determination of the analyte, such as glucose, concentration from the sample using, for example electrochemical, colorimetric, or photometric techniques, using an in vitro analyte test strip reader or meter (also referred to as a monitor, and the like). This technique is commonly referred to as in vitro or ex-vivo or discrete testing in that the analyte test strip is outside of the body of a user and the sample is removed or extracted from the body and applied to the test strip for analysis.

The components of in vitro analyte systems can vary, but may include a plurality of analyte test strips, such as provided in a test strip cartridge, a test strip meter used to read the test strip and a lancing device which may or may not be integrated with the meter. Examples include the FreeStyle® and Precision® brands of analyte testing systems from Abbott Diabetes Care Inc. of Alameda, Calif.

Also developed for analyte testing are continuous or in vivo monitoring systems in which at least a portion of an analyte sensor is positioned for a period of time beneath the skin of a user so as to be in direct contact with biological fluid during the period of time. Using such in vivo monitoring systems, analyte monitoring is achieved with the in vivo analyte sensor, transcutaneously positioned or wholly implanted, or otherwise maintained in fluid contact with the biological fluid over the period of monitoring time, and analyte-related signals are obtained semi-continuously or substantially continuously over a period of time at predetermined time intervals such as once every minute, or once every five minutes or longer or shorter, as opposed to at discrete time points as in the case of testing with in vitro systems, where the discrete time points are based on when the user decides to use the in vitro system.

The components of in vivo analyte systems can vary, but may include an in vivo analyte sensor, a sensor control unit configured for direct or indirect electrical contact with the in vivo sensor, and a receiver unit or monitor to receive communication from the sensor control unit, e.g., wirelessly by radio frequency (RF), infrared (IR), or the like, or with a wired connection using a cable. An example of a continuous glucose monitoring system includes the FreeStyle Navigator® continuous glucose monitoring system from Abbott Diabetes Care Inc. of Alameda, Calif.

Users of in vivo monitoring systems often continue to use in vitro analyte systems in conjunction with the in vivo monitoring system, e.g., to calibrate and/or confirm information obtained from the in vivo systems.

Users of either or both in vitro and in vivo analyte monitoring systems may be required to carry with them multiple system components, which is inconvenient. For example, sensor control units of in vivo monitoring systems may be configured to be positioned for a period of time on the body of a user either directly or using a mounting unit and in electrical communication with the in vivo analyte sensor, either of which may include an adhesive or other attachment feature for attachment to skin. However, one or more other components of the system may still need to be carried, such as the receiver unit which includes the user interface to output or present information to the patient or the user of the in vivo monitoring systems, as well as components of the in vitro analyte measurement system, if used. Furthermore, existing systems or system components carrying techniques are often cumbersome, fragile, and do not promote inconspicuous testing. There is also a need to prevent water or moisture from contacting one or more components of the system described above.

Accordingly, as analyte testing or monitoring outside of clinical settings continues to be of importance in health management, there is a need for carrying cases that provide a compact, convenient, and discrete way for a user to carry and use equipment necessary to conduct analyte testing or monitoring. Also of interest are carrying cases that protect a carried medical device from environmental factors such as water, moisture, contaminants, debris, or the like.

SUMMARY

Embodiments of the present disclosure include carrying cases and methods for carrying one or more portable medical devices or one or more components of medical devices or systems, e.g., medical devices used for analyte testing of a biological fluid, as well as methods of analyte testing.

Certain embodiments of the medical device carrying cases described herein include features to allow convenient visual and/or physical access to at least a portion of the carried medical device without having to remove the medical device from the carrying case. The subject cases are suitable for carrying, for example, portable analyte testing medical devices that include visual displays and/or integrated in vitro analyte test strip ports and/or other connections. Many embodiments include features such that a carried medical device may be accessed via an access portion of a closed carrying case without having to open the carrying case.

In certain embodiments, the medical device carrying case is configured to carry a medical device having an integrated in vitro analyte test strip port, and in one embodiment includes a housing having a first wall and a second wall, a connector portion that joins the first and second walls together to provide a cavity to accommodate a medical device having an integrated in vitro analyte test strip port, and an in vitro analyte test strip port access portion comprising a cut-out that is configured to permit passage of an in vitro analyte test strip therethrough.

An analyte meter carrying system in another aspect of the present disclosure includes an analyte meter comprising an integrated in vitro analyte test strip port and a user interface, and a water-tight carrying case comprising first and second walls that define a cavity to hold the analyte meter, wherein the carrying case is configured to allow manipulation of the user interface of the analyte meter from outside the carrying case when the analyte meter is in the carrying case.

Embodiments also include carrying cases and methods of carrying medical devices that provide a barrier between a carried medical device and the environment to prevent environmental factors from contacting the medical device, e.g., water tight or sealed carrying cases to prevent or minimize moisture or contaminants from contacting the medical device. Examples of medical devices that may be used with the carrying cases described herein include, but are not limited to, one or more components of an in vitro analyte testing system such as in vitro glucose meters, one or more components of in vivo analyte monitoring systems (e.g., receiver/display units) e.g., in vivo components that have integrated in vitro meters, and drug delivery pumps, including drug delivery pumps that have integrated in vivo analyte monitoring components and/or in vitro analyte components, and the like.

Certain embodiments include carrying cases having a housing having a first or frontal wall and an opposing second or rear wall. The two walls may be releasably coupled together by a connection portion to form a body having a hollow cavity shaped and dimensioned to accommodate and securely hold a medical device within the cavity. The connection portion may include a closeable fastener to selectively interconnect the first and second walls together. The closeable fastener may comprise an inter-engageable connector positioned about the perimeters of the first and second walls. The inter-engageable connector may comprise a zipper. The zipper may comprise dual sliders that move independently of each other.

In certain embodiments, at least a portion of the housing may comprise a material that permits manipulation of a user interface of the medical device carried in the carrying case from outside the carrying case. In particular embodiments, the frontal wall of the carrying case may be characterized as a user interface wall as it aligns with and covers a user interface of a carried medical device when the medical device is carried in the case. User interface features of a medical device include features that enable communication between (to and/or from) a user and the medical device, including one or more elements with which a user operates or uses the device or the component of the device in order to carry out analyte testing and include, but are not limited to, visual displays and/or actuators (by way of buttons, knobs, levers, wheels, touch screens, or the like). In certain embodiments, the user interface of the medical device is configured for operation or manipulation by the user while the medical device is in the case, e.g., through the viewing window of the carrying case. For example, the viewing window may include material that permits a user to manipulate the user interface of a carried medical device by contacting the viewing window which may be caused to contact or otherwise interact with a given user interface element. Embodiments of the carrying cases include a test strip port access portion that surrounds an in vitro test strip port of a medical device carried by the case.

Embodiments may also include an attachment member to attach a carrying case to a user, e.g., to clothing such as a belt or handbag. Attachment members may be secured, for example, to the second wall of the carrying case so that the user interface of the carrying case, and correspondingly the user interface of a carried medical device, may be accessible and viewable (when provided with a viewable interface) without removing the medical device from the carrying case, when the carrying case attachment member is attached to a user. Attachment members may also be secured so that an in vitro analyte test strip port of a carried medical device may be accessed with an in vitro analyte test strip without removing the medical device from the carrying case, when the carrying case attachment member is attached to a user.

The carrying case may comprise an in vitro analyte test strip port access portion that is configured to permit passage of an in vitro analyte test strip therethrough to engage with the test strip port of the medical device when the medical device is held in the carrying case. In certain embodiments, the in vitro analyte test strip port access portion may be immoveable, while in other embodiments, the in vitro analyte test strip port access portion may be moveable to selectable positions about the carrying case. The test strip port access portion may comprise a cut-out. The carrying case may comprise a covering or cap to seal the in vitro analyte test strip access portion.

The present disclosure also provides for methods involving the use of the medical device operatively carried within the subject carrying cases. Certain methods include testing for an analyte which may include positioning a medical device comprising a test strip port into a carrying case, inserting a test strip through a test strip access portion of the carrying case and into the test strip port of the medical device, and testing for a concentration of an analyte sample on the test strip using the medical device.

Other methods provided in the present disclosure include methods of fabricating the subject carrying cases which may involve an injection molding process including multiple injection steps. In certain methods, such a process includes injecting a first material into a carrying case mold to produce a case body defining a compartment for receiving the medical device, the case mold having at least one feature to provide a corresponding at least one void within the produced case body and injecting a second material into the carrying case mold to produce a user-accessible area at the at least one void of the case body, wherein the user-accessible area enables user access of the medical device when operatively positioned within the carry case. The first and second injecting steps may occur at different times or simultaneously. The first and second materials may have the same or different opacity and/or the same or different rigidity/flexibility. The user accessible areas may enable visibility of, or physical access to, the medical device (such as visibility of a display on the device or manipulation of interface keys, e.g., buttons on a user interface of the device). Such methods may also include three, four or more injecting steps of the same or different materials.

Another fabrication method of the present disclosure includes providing a carrying case mold having at least one void, providing a plug at the at least one void, injecting at least one material into the carrying case mold to produce a case body defining a compartment for receiving the medical device, and removing the plug to provide a cut-out within the resulting case body, wherein the cut-out is for physically accessing a portion of the medical device when operatively received within the compartment. In certain embodiments, the medical device comprises an integrated in vitro analyte test strip port which is accessible via the cut-out when the medical device is operatively received within the compartment.

These and other features, objects and advantages of the present disclosure will become apparent to those persons skilled in the art upon reading the details of the present disclosure as more fully described below.

INCORPORATION BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,676,819; 6,730,200; 6,736,957; 6,746,582; 6,749,740; 6,764,581; 6,773,671; 6,881,551; 6,893,545; 6,932,892; 6,932,894; 6,942,518; 7,167,818; and 7,299,082; U.S. Published Application Nos. 2004/0186365; 2005/0182306; 2007/0056858; 2007/0068807; 2007/0227911; 2007/0233013; 2008/0081977; 2008/0161666; and 2009/0054748; U.S. patent application Ser. No. 11/396,135, now U.S. Pat. No. 7,620,438; Ser. Nos. 11/537,984; 12/131,012; 12/242,823, now U.S. Pat. No. 8,219,173; Ser. No. 12/363,712, now U.S. Pat. No. 8,346,335; Ser. Nos. 12/698,124; 12/714,439; 12/807,278; 12/842,013; and 12/848,075, now U.S. Pat. No. 8,478,557.

BRIEF DESCRIPTION OF THE DRAWINGS

Referring now to the drawings, wherein like reference numerals and letters indicate corresponding structure throughout the several views:

FIG. 1A shows a frontal view of the medical device carrying case according to the present disclosure having an in vitro analyte test strip port access portion, FIG. 1B is a perspective view of the case of FIG. 1A showing the medical device securely fastened inside the case, FIG. 1C shows a rear view of the case of FIG. 1A having an attachment member in the form of a clip portion, and FIG. 1D is a view of the perimeter of the case of FIG. 1A in a closed state;

FIG. 4A shows an isometric, exploded view of the water-tight medical device carrying case; FIG. 4B shows a frontal view of the water-tight medical device carrying case in a water-tight sealed configuration; and FIG. 4C shows a side view of the water-tight medical device carrying case with an exploded view of a portion of a wall of the case.

DETAILED DESCRIPTION

Figure 1A:
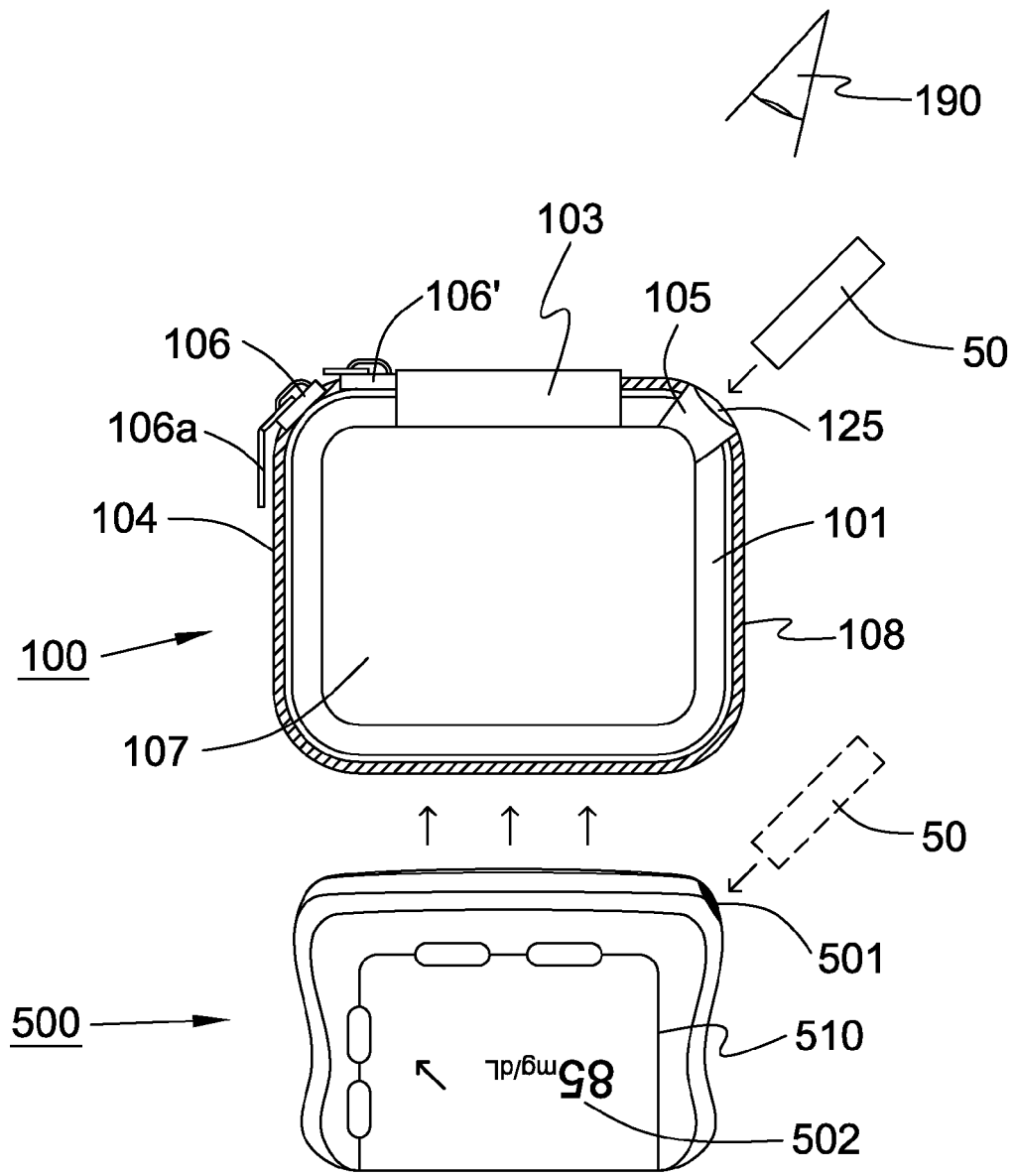
FIGS. 1A-1D show an exemplary embodiment of a medical device carrying case according to the subject disclosure, where

Before the present disclosure is further described, it is to be understood that the present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, exemplary methods and materials are now described. All publications mentioned herein are incorporated herein by reference to disclose and describe the methods and/or materials in connection with which the publications are cited.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

It is to be understood and will be apparent to those of skill in the art that the embodiments of the subject disclosure may be applicable to carrying a variety of medical devices, e.g., medical device components that include integrated in vitro analyte test strip ports. Certain embodiments of the carrying cases are configured to receive and securely hold or retain in vitro analyte meters (also referred to as single point monitors, single point blood glucose modules, blood glucose monitors or meters, and the like). Other embodiments are described with respect to carrying a component of an in vivo analyte monitoring system, e.g., that includes an integrated in vitro analyte testing system having an in vitro analyte test strip port (i.e., integrated in vivo analyte monitoring system components such as integrated in vivo analyte receiver unit housing that includes an in vitro test strip port). In particular, and in many embodiments, the in vitro analyte meters are combined with in vivo analyte monitoring systems to provide an integrated analyte monitoring system to monitor an analyte in vivo and/or in vitro.

Embodiments of carrying cases having integrated in vitro analyte test strip port access portions to align about and provide direct access to an in vitro analyte test strip port of a carried medical device are described. The in vitro analyte test strip port access portion may include a cut-out configured to accommodate an in vitro analyte test strip therethrough so that the in vitro analyte test strip is insertable into the in vitro analyte test strip port of the medical device carried by the carrying case without removal of the medical device from the carrying case. In many embodiments, the cut-out is the only opening or access point to the test strip port of a carried medical device when the carrying case is fully closed around the medical device. The in vitro analyte test strip port access portion of the carrying case may be positioned in a variety of positions about the carrying case, e.g., about the perimeter of the case. In certain embodiments, the in vitro analyte test strip port access portion is fixed in place on the carrying case (i.e., immovable), and in certain other embodiments the in vitro analyte test strip port access portion is moveable (e.g., slidable), about the carrying case to a plurality of selectable positions.

Embodiments of the subject carrying cases are suitable for use with standalone in vitro analyte meters. The components of in vitro analyte systems can vary, but may include a plurality of analyte test strips, such as provided in a test strip cartridge, a test strip meter used to read the test strip and a lancing device which may or may not be integrated with the meter. Examples of in vitro analyte systems are described, e.g., in U.S. Pat. No. 7,041,468 and in U.S. Publication Nos. 2010/0204557 and 2010/0198142, the disclosures of each of which are herein incorporated by reference for all purposes.

The subject carry cases are also suitable for us with in vitro meters which are integrated with a housing of a component of an in vivo system, e.g., integrated into a housing of an in vivo sensor control unit and/or an in vivo receiver unit, and/or an in vivo mounting unit, or other. In vivo analyte monitoring systems include, for example, an in vivo analyte sensor (e.g., glucose sensor, ketone sensor, etc.) that is configured to be at least partially implanted in a user and in contact with biological fluid for a period of time, to monitor the analyte level in the contacted biological fluid semi-continuously or continuously over the period of time. During this period of time of in vivo analyte monitoring, separate user initiated discrete in vitro testing may be performed. For example, analyte results obtained from in vitro testing may be used to calibrate the in vivo system and/or may be used to periodically confirm results of an in vivo system, e.g., prior to relying on the results obtained by the in vivo analyte system. In vivo analyte systems with integrated in vitro analyte systems such as integrated calibrators, including integrated in vitro analyte test strip ports, are described, e.g., in U.S. Pat. Nos. 4,545,382; 4,711,245; 5,262,035; 5,262,305; 5,264,104; 5,320,715; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,676,819; 6,730,200; 6,736,957; 6,746,582; 6,749,740; 6,764,581; 6,773,671; 6,881,551; 6,893,545; 6,932,892; 6,932,894; 6,942,518; 7,167,818; and 7,299,082; U.S. Published Application Nos. 2004/0186365; 2005/0182306; 2007/0056858; 2007/0068807; 2007/0227911; 2007/0233013; 2008/0081977; 2008/0161666; and 2009/0054748; U.S. patent application Ser. Nos. 12/131,012; 12/242,823, now U.S. Pat. No. 8,219,173; Ser. No. 12/363,712, now U.S. Pat. No. 8,346,335; Ser. Nos. 12/495,798; 12/495,803, now U.S. Pat. No. 8,346,337; and Ser. No. 12/495,807, now U.S. Pat. No. 8,465,425; Ser. Nos. 12/698,124; 12/714,439; 12/807,278; 12/842,013; and 12/848,075, now U.S. Pat. No. 8,478,557, the disclosures of each of which are herein incorporated by reference for all purposes.

Referring now to the figures and to FIGS. 1A-1D in particular, there is shown an embodiment of an analyte monitoring system including a medical device carrying case 100 that accommodates an in vitro analyte test strip 50 through a surface of the case, and a medical device 500.

Medical device 500 is shown in the embodiment of FIGS. 1A-1D as an in vivo analyte monitoring system component, and more specifically as a receiver unit of an in vivo analyte monitoring system such as in the form of a portable, hand-held pager-like receiver unit that receives analyte data from another component of an in vivo system. For example, such a receiver unit may be configured to communicate with a transmitter unit of an in vivo analyte system (not shown) such as a sensor control unit or the like (uni- or bi-directionally). Communication may be automatic (without any action to initiate transmissions other than initialization of the system and may be at least semi-continuous automatic broadcasts), or communication may be on-demand such that data communication only occurs upon action of a user to cause the data transfer such as requesting data transfer (see for example U.S. patent application Ser. Nos. 12/143,731, 12/143,734, 12/698,124, 12/730,193, and 12/807,278, the disclosures of which are herein incorporated by reference). Receiver unit 500 may include a user interface 510, and user interface 510 may include a display module 502. It is to be understood that receiver unit 500 may not include a user interface and/or may not include a display in certain embodiments.

Figure 1B:
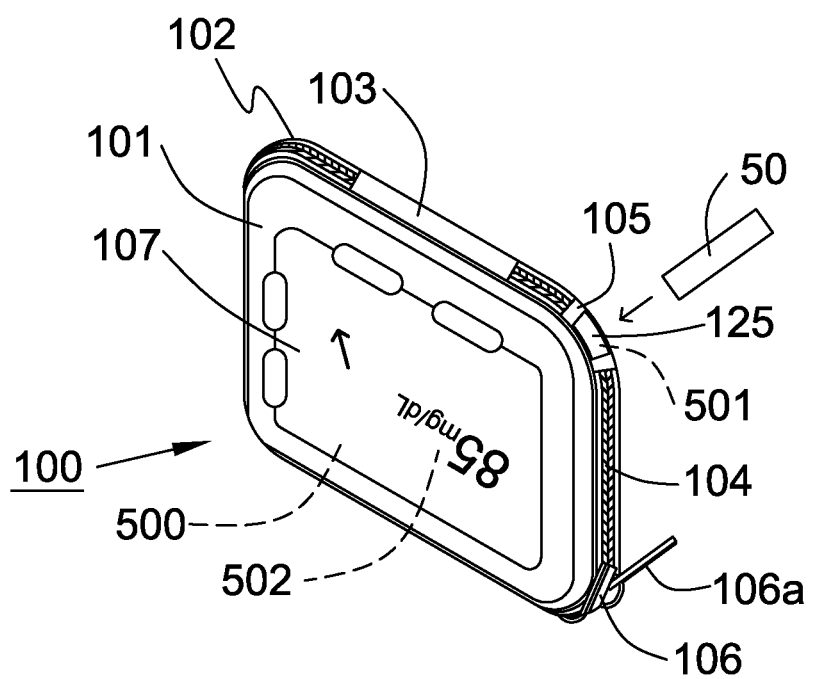

Medical device carrying case 100, according to one or more embodiments, includes a housing 108 having a frontal or first wall 101 and a second or rear or back wall 102 (the latter being best viewed in FIG. 1B). The two walls may be foldably or movably joined together at connector portion 103, and an in vitro analyte test strip port access portion 105 that includes a test strip aperture 125 configured to align with an in vitro test strip port 501 of a medical device 500, such as a component of an in vivo analyte system (or of an in vitro analyte meter that is not integrated in an in vivo system). Case 100 and port access portion 105 of the case are configured so that the in vitro analyte test strip port 501 of medical device 500 registers with the port access portion 105 upon positioning the medical device 500 within the case 100. Accordingly, when device 500 is held, positioned or carried within case 100, the aligned test strip port 501 of the in vivo system (or of an in vitro analyte meter that is not integrated in an in vivo system) is accessible through the in vitro analyte test strip port access portion 105 of the carrying case 100. FIG. 1A shows a frontal view orientation of medical device 500 and carrying case 100 in which medical device 500 is shown outside case 100 and oriented to be inserted into case 100 to register the integrated in vitro analyte test strip port 501 of the medical device 500 with in vitro analyte test strip port access portion 105 of the case. FIG. 1B shows medical device 500 securely fastened within case 100.

Port access portion 105 includes a cut-out or aperture 125 to provide access to a test strip port 501 of a medical device 500 inserted in case 100. Port access portion 105 may include an area, e.g., an area of a textile, elastomer, etc., that includes test strip aperture 125 to align with and substantially surround an in vitro analyte test strip port 501 of carried medical device 500 when positioned and secured within the case. Accordingly, cut-out 125 is dimensioned and positioned to permit entry of an in vitro analyte test strip 50 through cut-out 125 and into an in vitro test strip port 501 of medical device 500 when the medical device 500 is disposed in the cavity of the carrying case 100. Cut-out 125 may include a covering, e.g., a cap, a plug or the like, to cover cut-out 125 when not needed, e.g., between analyte testing with in vitro analyte test strips 50, and to provide access to an underlying test strip port 501 of an in vitro analyte meter 500 when uncovered. Access portion 105 may be positioned in any suitable location about the carrying case 100. In certain embodiments, access portion 105 is positioned on a side or perimeter portion of the case as shown in the embodiments of FIGS. 1A-1D, and in other embodiments it is positioned in a wall of the case 100.

Carrying case housing 108 defines a cavity or pocket into which medical device 500 may be positioned. Housing 108, at least in part, is defined by a first or frontal wall 101 and a second or rear wall 102, which may be opened and closed to provide access to and closure of the cavity so medical device 500 may be securely held within and removed from the housing 108. Walls 101 and 102 may be permanently and/or selectively interconnected to each other. In certain embodiments, the walls are interconnected by way of a fixed or permanent connector 103 that permanently connects front wall 101 and rear wall 102 together. Connector 103 includes one or more permanent attachment area(s) that join walls 101 and 102 together at at least one location along the walls' perimeter. In certain embodiments, walls 101/102 are further connectable around their peripheral edges to form the desired shape and interior cavity or pocket. The remainders of the perimeter of the walls 101/102 are inter-engageable and dis-engageable to open and close the case. Connector portion 103 may be flexible or rigid material such as a textile material, stitching, and the like, or may be an extension of one or both walls 101/102. Upon complete closure of the case 100 in many embodiments, access portion 105 may provide the only area of the case 100 through which an in vitro analyte test strip 50 may be accommodated for insertion therethrough. In certain embodiments, access portion 105 is formed by or upon inter-engaging walls 101 and 102 together. In certain embodiments, connector portion 103 may include access portion 105, and in certain other embodiments, port access portion 105 may be separate from, e.g., spaced apart from, connector portion 103.

Walls 101 and 102 may be further selectively interconnected about their perimeters with a closeable fastener such as an inter-engageable connector 104 provided around the periphery of the walls 101/102 in peripheral areas that lack connector portion 103 and/or access portion 105, such that the walls may be selectively inter-engaged together with the inter-engageable connector (see, e.g., FIGS. 1A-1D which show portions of the perimeter of case 100 closed with inter-engageable connector 104). The walls of the case may be selectively interconnected using any suitable inter-engageable connector, including, but not limited to, one or more of zippers, latches, snaps, inter-engaging hook and loop material (e.g., Velcro™, or the like), hooks, and the like, and combinations thereof.

Figure 1C:
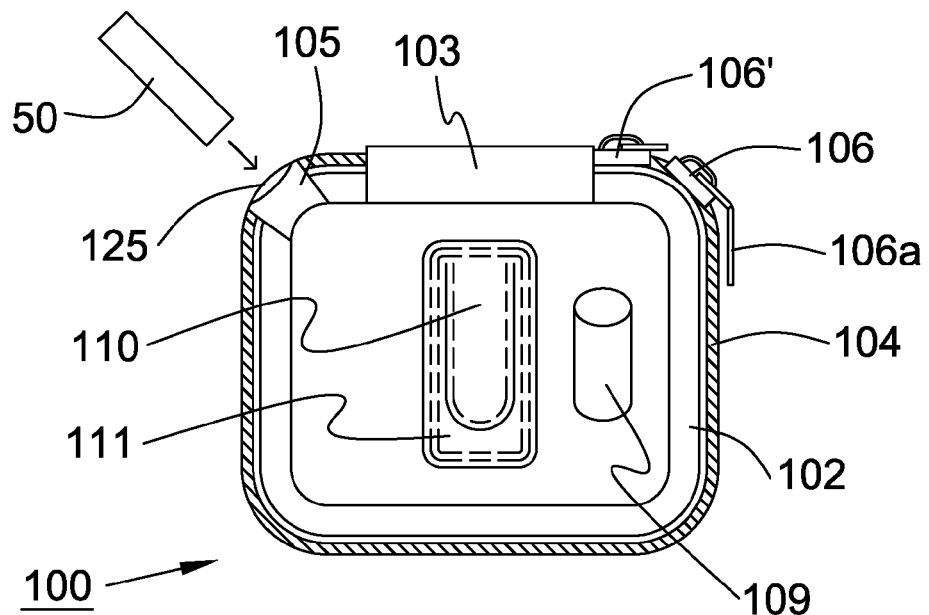
Figure 1D:
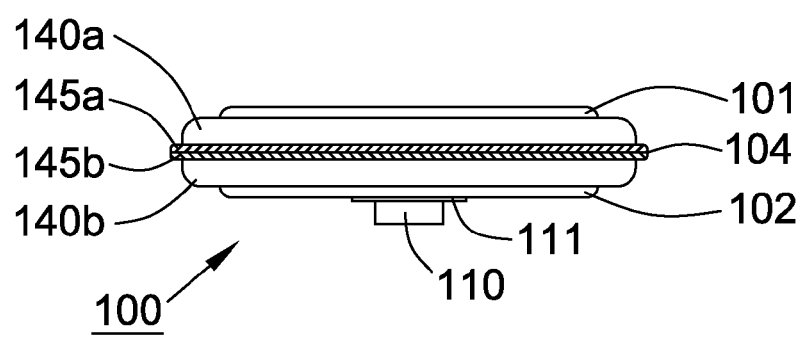

The embodiments of FIGS. 1A-1D show inter-engageable connector 104 in the form of a zipper unit. Zipper unit may extend partially or completely around the perimeter or edges of the carrying case, with the exception of connector portion 103 and/or in vitro analyte test strip port access portion 105 if such would prevent positioning of connector 104. As shown in FIG. 1D, zipper units may include a first closure panel 140*a* (e.g., a stringer) that includes first tape and teeth assembly 145*a* positioned about the periphery of first wall 101, and inter-engageable second closure panel 140*b* (e.g., a second stringer) that includes second tape and teeth assembly 145*b* positioned about the periphery of second wall 102. As shown in the figures, walls 101,102 have co-operable zipper teeth around their peripheries. At least one slider 106 is positioned on both first and second teeth assemblies, and the at least one slider 106 is moveable along the teeth assemblies to correspondingly engage/disengage the inter-engageable teeth assemblies (or uncouple the teeth assemblies). A slider may include a user-engageable tab 106*a*. One or more stops are included to maintain a slider on the teeth assemblies. Connector portion 103 and/or in vitro analyte test strip port access portion 105 may include a stop.

In certain embodiments, a zipper unit may include dual sliders. Dual sliders 106 and 106' are shown for example in the embodiment of FIGS. 1A and 1C. The dual sliders 106 and 106' move independently of each other to open and close the carrying case 100, and each may move in one or any direction about the carrying case 100. The dual sliders 106 and 106' are each positioned on both first and second teeth assemblies 145*a*/145*b* and are moveable along the panels in a clockwise and/or counterclockwise direction to cause connecting or disconnecting of the teeth assemblies 145*a*/145*b*, and therefore of the two walls 101/102 of the case. In certain embodiments, the dual sliders 106 and 106' are positioned adjacent to each other when the carrying case 100 is closed, and spaced apart when the carrying case 100 is opened to provide access to the internal cavity of the carrying case 100, for example for insertion or removal of medical device 500.

In certain embodiments, the carrying cases are constructed to position a carried medical device in a particular orientation with respect to a user to make using (e.g., viewing and/or test strip testing, etc.) convenient, for example by minimizing the amount of manipulation of the case and/or carried device. As shown in FIG. 1A, the components 100/500 of the system are oriented relative to each other so that case 100 can be clipped to an article of clothing (e.g., a belt, purse, or the like), and when medical device 500 is inserted into and secured in the case 100 so that in vitro analyte test strip port access 105 of the carrying case is aligned with the port 501 of receiver unit 500, the orientation of medical device 500 is such that the visual display module 502 of the receiver/display unit is upside down or inverted relative to the user 190 when the case is attached to, e.g., a belt, and the user 190 is looking downward at the system 100/500. More particularly, case 100 may be constructed so that second wall 102 is closest to a user's body when the case is attached to the user, e.g., to a user's belt, and frontal wall 101 faces away from user's body. In this manner, a user is able to view device display 502 in a convenient "right side up" orientation by grasping case 100 having medical device 500 therein and pivoting it upwards towards the user's field of vision while the case remains clipped to the clothing. When so pivoted, display module 502 will be "right side up" to the user. This described positioning of the medical device 500 in the case and orientation relative to a user 190 is exemplary only as a variety of orientations are envisioned.

In certain embodiments, frontal wall 101 includes an optional window 107, for viewing a user interface 510 of carried medical device 500 such as a visual display 502, or the like. Window 107 may be an opening in wall 101, or may include a transparent shroud, e.g., a transparent material, e.g., a transparent plastic or the like, and may be flexible or rigid. A transparent shroud may be any suitable material, e.g., scratch resistant and/or moisture resistant material.

FIG. 1C shows a planar view of second or rear or back wall 102 of case 100. Rear wall 102 includes an attachment member 110 in this embodiment. Attachment member 110 is mounted to wall 102 by a mount 111 or may be part of wall 102, e.g., an extension thereof, sewn in place, etc., and is removably attachable to an article of clothing such as a belt. Attachment member 110 may be permanently attached to wall 102, or may be attachable to and removable from the case 100 by a user. Attachment member 110 may include a clip portion. For example, an attachment member may include a first leg portion attached to rear wall 102, connected to a second leg, e.g., by a transition portion (e.g., a U-shape transition or the like). The second leg may be biased towards rear wall 102. An article of clothing may be positioned between the first and second legs to attach case 100 to the article of clothing. Attachment members include, but are not limited to, S-clips, U-clips, and the like. An attachment member 110 may include one or more barbs for securement to clothing. In certain embodiments, case 100 may be swivelable. For example, the connection between the case 100 and the attachment member 110 may allow the case 100 to swivel about a swivel point. A swivel attachment member 110 may therefore be configured to be attachable to an article of clothing and to a medical device carrying case 100 to permit the carrying case 100 to swivel about a swivel point from about 0° to about 360°, e.g., from about 0° to about 180° in certain embodiments. In certain embodiments, a locking mechanism is included to permit carrying case to selectively swivel and lock in a variety of pre-selected positions, e.g., anywhere between about 0° to about 360°, for ease of use and movement until a user adjusts the case to another position (e.g., by a light push of a finger), for example. Such attachment systems may include a ratchet and pawl, high friction rotary joints, or the like. The attachment member 110 may include a release button (not shown) for selectively coupling and releasing the case 100 and the attachment member 110.

As further shown in FIG. 1C, in certain embodiments, case 100 may include storage area 109 such as located on the front 101 and/or rear 102 walls (in or on an interior and/or exterior surface of one or both of the walls 101/102), to hold components for use with medical device 500, e.g., one or more components of an analyte testing system such as new and/or used test strips and/or new and/or used lancets and/or lancing devices and/or control solutions and/or drug administration devices (e.g., syringes, pen-type injectors, and the like).

Front and rear walls 101/102 may be any suitable material. The walls may include the same or different material, or may include some same and some different materials. The walls 101/102 may be flexible or rigid, and may include some flexible and some rigid material, e.g., a given wall may include one or more materials of differing softness/hardness. One or both of walls 101 and 102 may include flexible, deformable material, e.g., a textile, or the like. In certain embodiments, material may include a flexible and/or crushable and/or water proof material. In certain embodiments, the case is constructed of a substantially deformable material which is capable of absorbing shock delivered to the case. Examples of materials that may be employed include, but are not limited to, fabric, plastic, leather, elastic, nylon, neoprene, e.g., neoprene rubber secured between two layers of nylon, etc., and combinations thereof. In certain embodiments, case 100 or portions thereof are rigid and include hard material such as rigid plastic, or one or more polymers. For example, at least the perimeter of aperture 125 may include a material that is easy to disinfect, e.g., a hard elastomeric material or the like.

Figure 2:
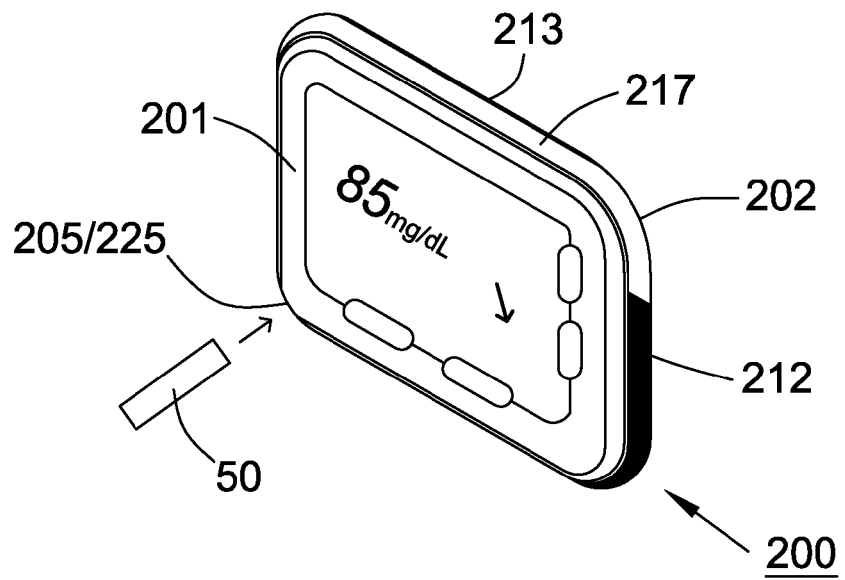
FIG. 2 shows a perspective view of an exemplary embodiment of a medical device carrying case according to the subject disclosure having a deformable side wall.

FIG. 2 shows another embodiment of a carrying case 200 that includes one or more stretchable side or peripheral walls 212 that join at least a portion of the peripheries of front and rear walls of the carrying case together. The stretchable side walls are configured to stretch, e.g., may include a stretchable textile such as an elastic material, or the like. As shown in FIG. 2, similar to case 100 of FIGS. 1A-1D, case 200 includes first and second walls 201/202, and in vitro analyte test strip port access portion 205 having a cut-out 225 to provide access to a test strip port of a medical device inserted in case 200. However, in this embodiment, walls 201 and 202 are joined about a portion of their peripheries by stretchable side wall 212. A portion of the periphery of the carry case includes a clearance 217 which is void of any stretchable side wall and which is dimensioned to permit insertion and removal of a medical device into case 200, and specifically between walls 201 and 202. Insertion of a medical device, such as by way of clearance 217, may cause stretchable side walls to stretch or expand so that a medical device is secured within the walls of the case as the stretchable side walls relax back upon the medical device to restrain the medical device within case 200. For example, the act of insertion of a medical device may cause expansion of the side walls and accommodation of the device into the case. In certain embodiments case 200 may include one or more of a lip 213, e.g., a rigid lip, to further secure a medical device in the case by providing a raised barrier. Rigid lip 213 may extend around all or part of periphery of case 200. Test strip access portion 205 and cut-out 225 may be omitted in certain embodiments and clearance 217 may serve as a test strip port access portion.

Figure 3:
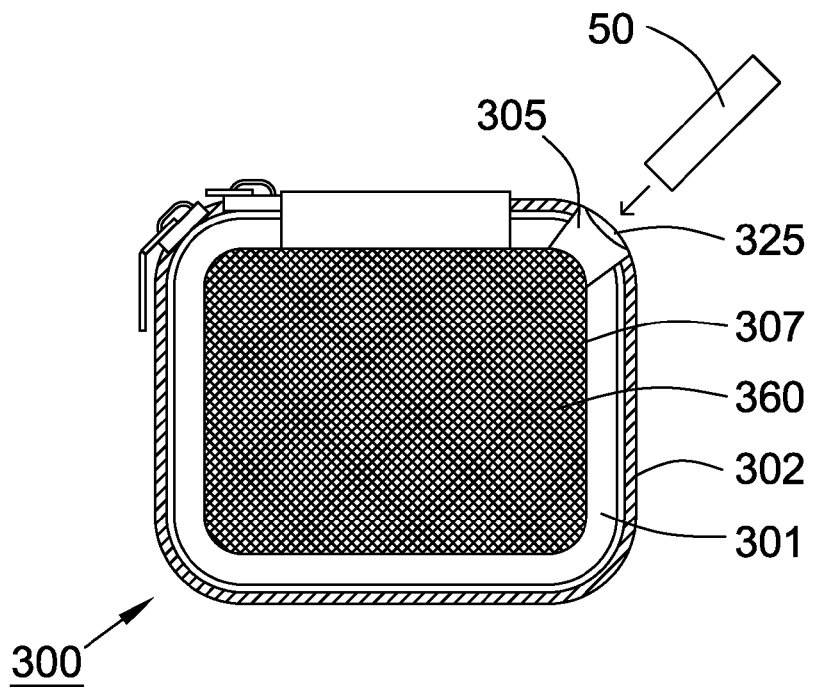
FIG. 3 shows a frontal view of an exemplary embodiment of a medical device carrying case according to the subject disclosure having a privacy shroud to releasably shroud at least a portion of the carrying case.

FIG. 3 shows an embodiment of a medical device carrying case 300 that includes a removable privacy shroud 360 to cover a window 307 of the carrying case 300. For example, shroud 360 may be opaque. As shown in FIG. 3, similar to cases 100 and 200 of FIGS. 1A-1D and 2, case 300 includes first and second walls 301/302, and in vitro analyte test strip port access portion 305 having a cut-out 325 to provide access to a test strip port of a medical device inserted in case 300. Shroud 360 is positioned proximate to window 307 and is selectively activateable to substantially cover and/or protect window 307, and in certain embodiments may assist in restraining a medical unit within the case. Shroud 360 may also protect the interior of carrying case 300 (and retained medical device) from environmental elements, e.g., if window 307 is an opening to the interior of the case.

Figure 4A:
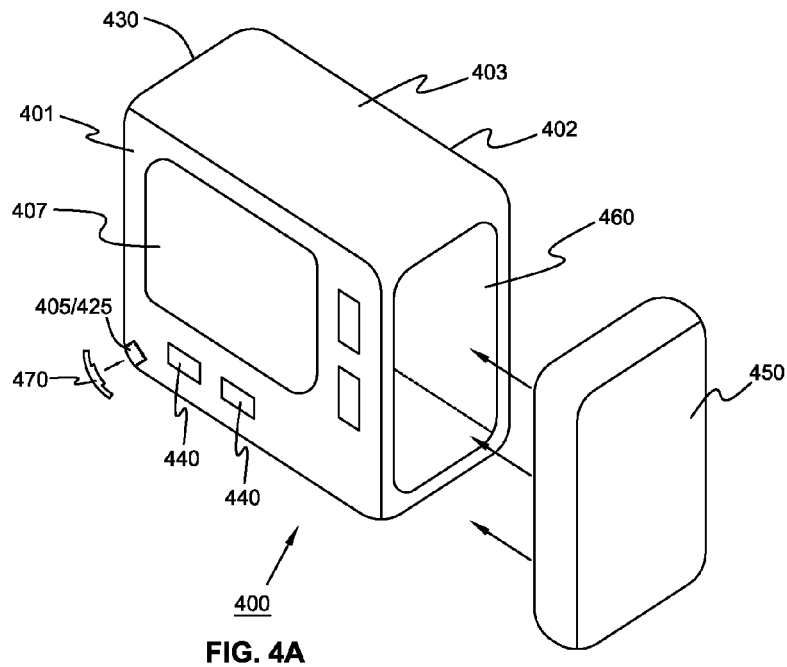
FIGS. 4A-4C show a rear view of an exemplary embodiment of a water-tight medical device carrying case according to the subject disclosure, where
Figure 4B:
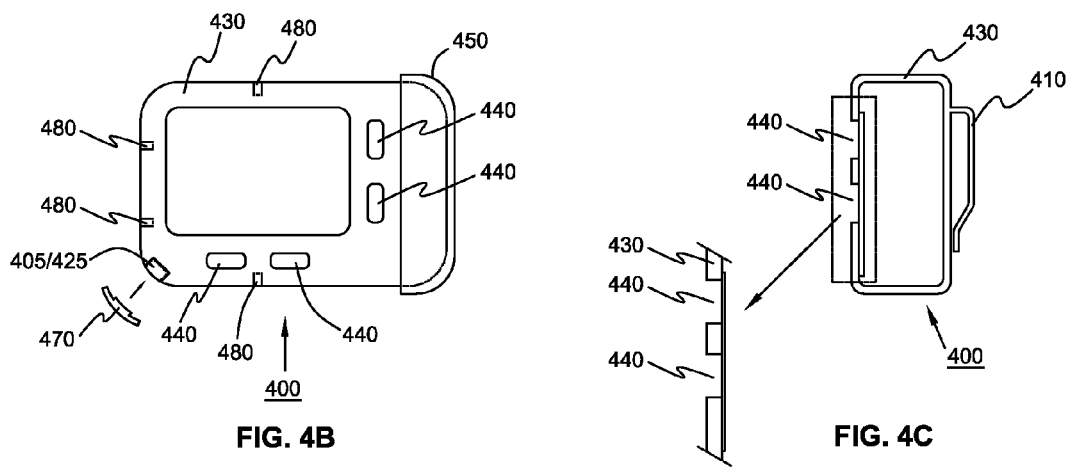
Figure 4C:
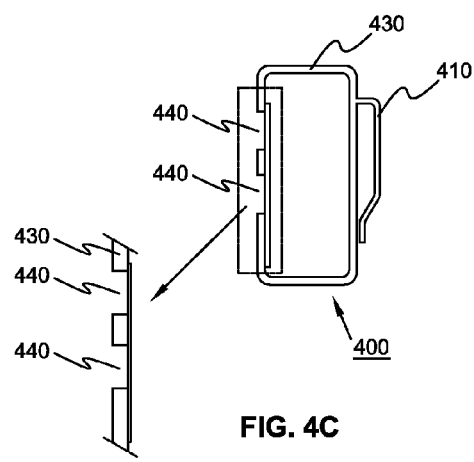

FIGS. 4A-4C show an embodiment of a water proof medical device carrying case 400 that includes a body 430 and mateable cap 450, which when coupled together provide a water tight seal. Carrying case 400 provides a compartment 460 formed by first or frontal wall 401 and second or rear wall 402 and side wall connector portion 403, which may be rigid in many embodiments, to house a medical device and protect it from environmental factors such as water, debris, etc. Carrying case 400 may be clear or opaque (e.g., injection or blown) and may be flexible or rigid, or include flexible portion(s) and rigid portion(s). For example, rigid portions may be used to protect a medical device held inside and flexible portions may be used to allow manipulation of the device from outside the case. Body 430 may include one or more features 480, such as bosses, (FIG. 4C) that may also be molded, to help position a medical device in the case.

While the illustrated embodiment of FIGS. 4A-4C shows cap 450 as a separate piece, cap 450 may be integrated or attached to case body 430 at an attachment point, e.g., with a hinge or the like. Accordingly, when cap 450 is coupled (e.g., using a snap fit, friction fit, interference fit, or the like, including combinations thereof) onto body 430, the carrying case is sealed to provide watertight protection for a medical device sealed therein. The sealed medical device may be operated from outside the case, and may be worn in water. Cap 450 and/or body 430 may include a sealing member, e.g., an elastomeric sealing member such as an elastomeric gasket, lip, ledge including overlapping edge, ridge, material interface, viscous sealant, and the like, or combinations.

If case 400 includes an in vitro analyte test strip port access portion 405 that includes a cut-out 425, a covering 470, such as an insertable plug, may be provided and dimensioned to be coupled with the cut-out 425 to close the cut-out 425 to provide a water-tight seal of the cut-out 425. Covering 470 and/or cut-out 425 may include a sealing member, e.g., an elastomeric sealing member such as an elastomeric gasket or the like. The covering 470 is shown as a separate piece, but may be attached about the cut-out 425 at an attachment point, e.g., with a hinge or the like.

In certain embodiments, a multi-shot injection molding process may be employed to produce case 400. Such a process includes at least first and second shots or injections of one or more types of materials, which may occur independently or simultaneously and without regard to ejection of the finished carrying case. This process is particularly useful if it is desired to have the case body 430 and one or more other portions of the case, such as a window 407 or button holes 440, made of different materials. For example, the case body 430 may be made of an opaque material and/or a rigid material that does not permit activation, i.e., does not enable visibility or physical manipulation, of a carried medical device, while the activation permissible areas of the case, i.e., window 407 and button holes 440, may include a transparent and/or flexible material. In such a process, a mold is provided having a shape, dimensions and features, e.g., cut-outs, openings, voids, bosses 480, plugs, etc., of the carry case to be produced. For example, as shown in FIG. 4C, the mold may be designed to include a shaped receptacle to receive material to form an attachment member 410 on an exterior surface of case body 430. Other voids or depressions in the case mold may be provided to form a corresponding shaped void or opening in case body 430, which voids and openings are then used to make other desired features, e.g., window 407, button holes 440, etc., of the resulting finished carrying case. Where the void or opening in the mold is to provide a corresponding opening in the finished carrying case, i.e., which opening is to remain clear of any injectable material, a temporary or removable plug or covering may be provided in the mold to prevent the ingress of material in its fluid or injectable state. For example, in order to maintain the test strip access portion cut-out 425 free of debris during the injection molding process, a temporary plug or covering may be used which may later be replaced by plug or covering 470 for use with the finished carrying case.

In one embodiment, a first shot of a material may be injected or blown into a carrying case mold to provide the structure defining the case body 430, and a second shot of a material may then be injected or blown into the mold to produce a window or lens 407 (e.g., a clear window) to enable visibility to a medical device held within the compartment 460 formed by the case body 430. In certain embodiments, the first injected material, i.e., that used to form the case body 430, may be made of an opaque or non-transparent, rigid material, e.g., a hard plastic, to ensure the structural integrity of the contained medical device. In order to provide the device viewing window or lens 407, the second injected material may be clear or transparent, e.g., a thermoplastic elastomer, or silicone, or the like. The mold may also be configured to provide a carrying case having access holes or voids 440 for receiving or covering or registering with user interface keys or buttons provided on a user interface surface of the medical device to be carried within the finished case in order to allow the buttons to be pushed from outside the case. In which case, the second shot of material, if also soft or flexible, may be used to make these features or overmoldings 440 to accommodate the user interface features. The area of the button hole(s) 440 may have a thickness that is less than the thickness of case body 430, at least adjacent surrounding areas of the holes, and in certain embodiments may be thinner than the entirety of the material of the case body, oftentimes thinner than window area 407 as well. If both the case and the lens are to be made of a rigid and transparent material, then only a single shot of material may be necessary, with the second shot of material used exclusively to form the overmoldings 440 for the user interface features. In still another embodiment, if the case body 430 is to be formed of a colored or opaque material, regardless of whether the material is rigid or compliant, and the lens is be required to be rigid and transparent, with the overmolding features 440 required to be made of a clear, soft material, then the case fabrication process may require at least three injections or shots, each of a different kind of material. It is noted that any two or more of the case components, including the case body, window/lens, overmoldings and/or plugs/coverings, may be separately molded and subsequently welded together to provide a finished assembly that is sealed water-tight.

Figure 5A:
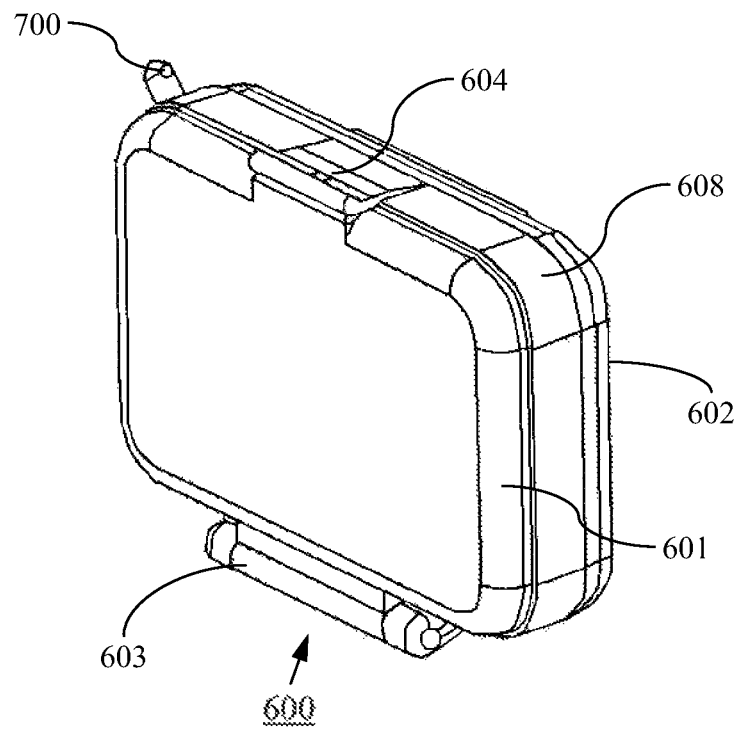
FIGS. 5A-5B show another exemplary embodiment of a medical device carrying case according to the subject disclosure.
Figure 5B:
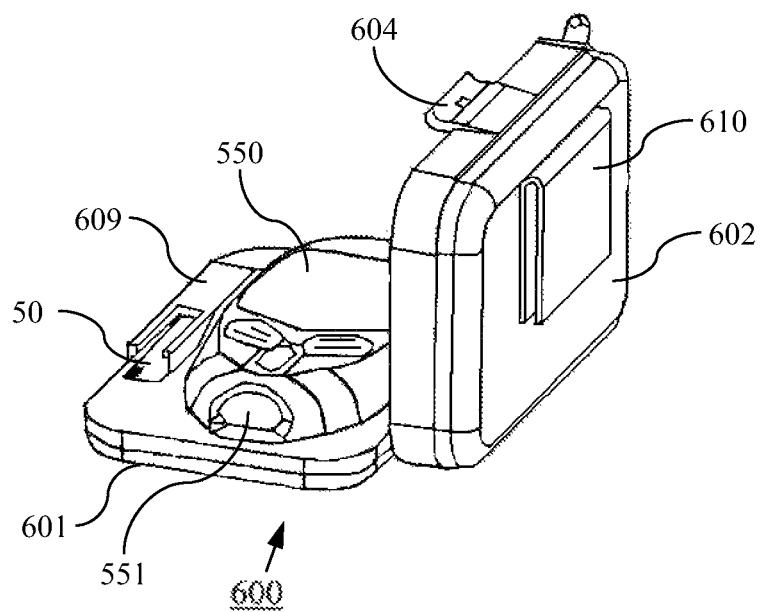

FIGS. 5A and 5B show another exemplary embodiment of a medical device carrying case 600 according to the subject disclosure. In many embodiments, case 600 is at least water resistant and in certain embodiments is water tight when closed.

FIG. 5A shows a frontal view of case 600 in a closed configuration. Case 600 includes housing 608, which may be flexible and/or deformable and/or rigid. Housing 608 includes a frontal or first wall 601 joined with second or rear or back wall 602 at connector portion 603. Connector portion 603 may be in the form of a hinge, or the like. The motion may be limited, e.g., to about 90° (or more or less in certain embodiments), so that when case 600 is positioned on an article of clothing such as a belt, and is open, the face of the medical device carried thereby is up towards the user face. An in vitro analyte test strip port access portion with a cut-out (not shown) may be provided in certain embodiments. Also a lanyard connector 700 for attaching a lanyard (not shown) may be included. In certain embodiments, housing 608 also includes inter-engageable connector 604 that may be a snap fit assembly so that the first wall 601 may be releasably joined to the second wall 602 by the snap-fit. A snap fit assembly may be a planar snap fit assembly, torsion snap fit assembly, annular snap fit assembly, cantilever snap fit assembly, and the like. A sealing member may be provided.

FIG. 5B shows a rear perspective view of case 600 in an open configuration. Attachment member 610 is mounted to back wall 602. Also shown is the interior space of housing 608 with a medical device 550, herein shown as an in vitro analyte testing meter, having a test strip port 551. In certain embodiments, case 600 may include storage area 609 such as shown in the interior space of the case to hold one or more analyte test strips 50 and/or lancing device (not shown), and/or other components used to carry out analyte testing.

In certain embodiments of the present disclosure, a medical device carrying case for carrying an encased medical device having an integrated in vitro analyte test strip port may comprise a housing having a first wall and a second wall, a connector portion that joins the first and second walls together to provide a compartment to accommodate a medical device having an integrated in vitro analyte test strip port, and an in vitro analyte test strip port access portion provided in the housing, the test strip port access portion comprising a cut-out that is configured to permit passage of an in vitro analyte test strip therethrough.

One aspect may further comprise a closeable fastener to selectively interconnect the first and second walls together.

In another aspect, the closeable fastener may comprise an inter-engageable connector positioned about the perimeters of the first and second walls.

In another aspect, the inter-engageable connector may comprise a zipper.

In yet another aspect, the zipper may comprise dual sliders that move independently of each other.

In another aspect, the in vitro analyte test strip port access portion may be immoveable.

In another aspect, the in vitro analyte test strip port access portion may be moveable to selectable positions about the carrying case.

In yet another aspect, the carrying case may comprise a transparent window to permit viewing of the medical device carried in the carrying case.

In another aspect, the transparent window may be made of a material that permits manipulation of a user interface of the medical device carried in the carrying case from outside the carrying case.

In another aspect, at least a portion of the housing may comprise a material that permits manipulation of a user interface of the medical device when carried in the carrying case from outside the carrying case.

Another aspect may further comprise an attachment member to attach the carrying case to an article of clothing.

In one aspect, the attachment member is configured to enable the case to be swivelable.

Another aspect may further comprise a covering to provide a water-tight seal about the cut-out.

In certain embodiments of the present disclosure, an analyte meter carrying system may comprise an analyte meter comprising an integrated in vitro analyte test strip port and a user interface, and a carrying case comprising first and second walls that define a cavity to hold the analyte meter, wherein the carrying case is configured to allow manipulation of the user interface of the analyte meter from outside the carrying case when the analyte meter is in the carrying case.

In one aspect, the carrying case may comprise a test strip port access portion that is configured to permit passage of an in vitro analyte test strip therethrough to engage with the in vitro analyte test strip port of the analyte meter when the analyte meter is in the carrying case.

In another aspect, the test strip port access portion may comprise a cut-out.

In another aspect, the carrying case may comprise a covering to seal the test strip access portion.

In one aspect, the analyte meter may be a component of an in vivo analyte monitoring system.

In another aspect, the analyte meter may be integrated with an in vivo analyte monitoring system receiver unit.

In yet another aspect, the carrying case may further comprise a stretchable side wall interconnecting the first and second walls.

In certain embodiments of the present disclosure, a method of testing for an analyte may comprise positioning a medical device comprising a test strip port into a carrying case, inserting a test strip through a test strip access portion of the carrying case and into the test strip port of the medical device, and testing for an analyte using the test strip.

One aspect may further comprise removing a covering from the test strip access portion of the carrying case prior to inserting the test strip.

In another aspect, positioning the medical device into the carrying case may comprise expanding a stretchable portion of the carrying case.

Another aspect may further comprise manipulating a user interface of the medical device from outside the carrying case.

In certain embodiments of the present disclosure, a method of fabricating a carrying case for a medical device may comprise injecting a first material into a carrying case mold to produce a case body defining a compartment for receiving the medical device, the case mold having at least one feature to provide a corresponding at least one void within the produced case body, and injecting a second material into the carrying case mold to produce a user-accessible area at the at least one void of the case body, wherein the user-accessible area enables user access to the medical device when operatively positioned within the carry case.

In one aspect, injecting the first material and injecting the second material may occur independently of each other.

In another aspect, injecting the first material and injecting the second material may occur simultaneously.

In one aspect, the user-accessible area may enable visibility of the medical device.

In one aspect, the second material may be a transparent material.

In another aspect, the medical device may include a display and wherein the user-accessible area of the carrying case is configured to substantially align with the display of the medical device when the medical device is operatively positioned within the compartment.

In certain aspects, the user-accessible area may enable manipulation of the medical device.

In another aspect, the second material may be a flexible material.

In one aspect, the second material may have a thickness that is less than the thickness of the first material.

In one aspect, the medical device may include a user interface and wherein the user-accessible area of the carrying case is configured to substantially align with the user interface when the medical device is operatively positioned within the compartment.

In another aspect, the user interface may include input keys and wherein the user-accessible area includes receptacles positioned for aligning with the input keys.

In another aspect, the second material may include a thermoplastic elastomer.

In another aspect, the first material may include a rigid plastic material.

In another aspect, the first material and the second material may be waterproof.

In one aspect, injecting the second material may provide a water-tight seal between the case body and the user-accessible area.

One aspect may further comprise injecting a third material into the carrying case mold.

In one aspect, injecting the third material may produce a second user-accessible area of the medical device at at least one void.

Another aspect may further comprise providing a sealing member for enclosing the compartment to provide a water-tight carrying case.

Another aspect may further comprise forming an attachment member on an exterior surface of the case body, the attachment member configured to attach the carrying case to an article of clothing.

In one aspect, injecting the first material may form the attachment member.

Certain embodiments of the present disclosure include a method of fabricating a carrying case for a medical device comprising providing a carrying case mold having at least one void, providing a plug at the at least one void, injecting at least one material into the carrying case mold to produce a case body defining a compartment for receiving the medical device, and removing the plug to provide a cut-out within the resulting case body, for physically accessing a portion of the medical device when the medical device is operatively received within the compartment.

In one aspect, the medical device may comprise an integrated in vitro analyte test strip port which is accessible via the cut-out when the medical device is operatively received within the compartment.

The carrying cases described herein may be any suitable shape to provide a secure fit for a particular medical device, and may vary depending on the shape of the medical device to be carried thereby. In the embodiments illustrated herein, the carrying cases are shown as substantially rectangular in shape, however other shapes are contemplated as well. The carrying cases are shaped and dimensioned to provide a body having contours corresponding generally to the contours of a medical device to be carried therein.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in the appended claims, the singular forms "a", "an", "said", and "the" include plural referents unless the specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation. Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Stated otherwise, unless specifically defined herein, all technical and scientific terms used herein are to be given as broad a commonly understood meaning as possible while maintaining claim validity.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:

1. A medical device carrying case for carrying an encased medical device having an integrated in vitro analyte test strip port, the carrying case comprising:
    a housing having a first wall and a second wall;
    a connector portion that joins the first and second walls together to provide a compartment to accommodate a medical device having an integrated in vitro analyte test strip port;
    an in vitro analyte test strip port access portion provided in the housing, the test strip port access portion comprising a cut-out that is configured to permit passage of an in vitro analyte test strip therethrough; and
    a covering to provide a water-tight seal about the cut-out.

2. The carrying case of claim 1, further comprising a closeable fastener to selectively interconnect the first and second walls together.

3. The carrying case of claim 2, wherein the closeable fastener comprises an inter-engageable connector positioned about perimeters of the first and second walls.

4. The carrying case of claim 3, wherein the inter-engageable connector comprises a zipper.

5. The carrying case of claim 4, wherein the zipper comprises dual sliders that move independently of each other.

6. The carrying case of claim 1, wherein the in vitro analyte test strip port access portion is immoveable.

7. The carrying case of claim 1, wherein the in vitro analyte test strip port access portion is moveable to selectable positions about the carrying case.

8. The carrying case of claim 1, further comprising a transparent window to permit viewing of the medical device carried in the carrying case.

9. The carrying case of claim 8, wherein the transparent window is made of a material that permits manipulation of a user interface of the medical device carried in the carrying case from outside the carrying case.

10. The carrying case of claim 1, wherein at least a portion of the housing comprises a material that permits manipulation of a user interface of the medical device when carried in the carrying case from outside the carrying case.

11. The carrying case of claim 1, further comprising an attachment member to attach the carrying case to an article of clothing.

12. The carrying case of claim 11, wherein the attachment member is configured to enable the carrying case to be swivelable.

13. An analyte meter carrying system, the system comprising:
    an analyte meter comprising an integrated in vitro analyte test strip port and a user interface; and
    a carrying case comprising first and second walls that define a cavity to hold the analyte meter, wherein the carrying case is configured to allow manipulation of the user interface of the analyte meter from outside the carrying case when the analyte meter is in the carrying case;
    wherein the carrying case comprises a test strip port access portion that is configured to permit passage of an in vitro analyte test strip therethrough to engage with the integrated in vitro analyte test strip port of the analyte meter when the analyte meter is in the carrying case; and further wherein the carrying case comprises a covering to seal the test strip port access portion.

14. The system of claim 13, wherein the test strip port access portion comprises a cut-out.

15. The system of claim 13, wherein the analyte meter is a component of an in vivo analyte monitoring system.

16. The system of claim 15, wherein the analyte meter is integrated with an in vivo analyte monitoring system receiver unit.

17. The system of claim 13, wherein the carrying case further comprises a stretchable side wall interconnecting the first and second walls.

18. A method of testing for an analyte, the method comprising:

positioning a medical device comprising a test strip port into a carrying case;

inserting a test strip through a test strip access portion of the carrying case and into the test strip port of the medical device;

removing a covering from the test strip access portion of the carrying case prior to inserting the test strip, wherein the covering provides a water-tight seal prior to being removed from the test strip access portion; and testing for an analyte using the test strip.

19. The method of claim 18, wherein positioning the medical device into the carrying case comprises expanding a stretchable portion of the carrying case.

20. The method of claim 18, further comprising manipulating a user interface of the medical device from outside the carrying case.

* * * * *